United States Patent
dos Santos Silva et al.

(10) Patent No.: US 11,635,814 B2
(45) Date of Patent: Apr. 25, 2023

(54) PREVENTING ACCESS TO POTENTIALLY HAZARDOUS ENVIRONMENTS

(71) Applicant: INTERNATIONAL BUSINESS MACHINES CORPORATION, Armonk, NY (US)

(72) Inventors: Bruno dos Santos Silva, McKinney, TX (US); Diogo Tadeu Silva de Araujo, Cedar Park, TX (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 880 days.

(21) Appl. No.: 16/521,734

(22) Filed: Jul. 25, 2019

(65) Prior Publication Data
US 2021/0026448 A1    Jan. 28, 2021

(51) Int. Cl.
*G06F 3/01* (2006.01)
*G10L 15/18* (2013.01)
(Continued)

(52) U.S. Cl.
CPC .............. *G06F 3/015* (2013.01); *A61B 5/375* (2021.01); *A61B 5/7282* (2013.01);
(Continued)

(58) Field of Classification Search
CPC ....... G06F 3/015; A61B 5/375; A61B 5/7282; A61B 5/165; A61B 5/4809; G10L 15/22; G10L 2015/225
See application file for complete search history.

(56) References Cited

U.S. PATENT DOCUMENTS 6,167,298 A * 12/2000 Levin .................. A61B 5/6803
600/545
6,633,235 B1   10/2003 Hsu et al.
(Continued)

FOREIGN PATENT DOCUMENTS

WO        2017166825 A1    10/2017

OTHER PUBLICATIONS

Mell et al., "The NIST Definition of Cloud Computing", Recommendations of the National Institute of Standards and Technology, NIST Special Publication 800-145, Sep. 2011, 7 pages.
(Continued)

*Primary Examiner* — Mark Villena
(74) *Attorney, Agent, or Firm* — Andre L. Adkins

(57) ABSTRACT

A method, computer system, and a computer program product for managing a plurality of electronic devices controlling access to one or more hazards in a physical environment. The present invention may include detecting a plurality of brain-wave patterns associated with a user. The present invention may then, in response to detecting motion of the user and the plurality of brain-wave patterns associated with the user matching a pattern, include operating at least one electronic device to disable access to a corresponding hazard. The present invention may further include operating the at least one electronic device to enable access to the corresponding hazard based on receiving input from the user to enable the at least one electronic device, wherein the input being received from the user is in response to prompting the user to correctly respond to a question previously answered by the user.

20 Claims, 5 Drawing Sheets

(51) Int. Cl.
*G10L 15/22* (2006.01)
*A61B 5/00* (2006.01)
*G10L 17/24* (2013.01)
*A61B 5/375* (2021.01)

(52) U.S. Cl.
CPC .......... *G10L 15/1822* (2013.01); *G10L 15/22* (2013.01); *G10L 17/24* (2013.01); *G10L 2015/225* (2013.01); *G10L 2015/227* (2013.01)

(56) References Cited

U.S. PATENT DOCUMENTS

| | | | |
|---|---|---|---|
| 6,874,265 B1 | 4/2005 | Pathak | |
| 7,855,652 B1 | 12/2010 | Giovannelli et al. | |
| 8,165,867 B1 | 4/2012 | Fish | |
| 8,725,842 B1 | 5/2014 | Al-Nasser | |
| 9,230,560 B2 | 1/2016 | Ehsani et al. | |
| 9,384,644 B1 | 7/2016 | McWilliams | |
| 9,497,307 B2 | 11/2016 | Jiang | |
| 10,647,333 B1* | 5/2020 | Donnelly | B60K 35/00 |
| 2004/0083092 A1 | 4/2004 | Valles | |
| 2014/0221779 A1 | 8/2014 | Schoonover et al. | |
| 2016/0078354 A1* | 3/2016 | Petri | G06N 5/02 706/50 |
| 2016/0093207 A1* | 3/2016 | Di Censo | H04R 1/1091 340/944 |
| 2016/0174913 A1 | 6/2016 | Somanath et al. | |
| 2016/0343241 A1* | 11/2016 | Rossi | G08B 29/126 |
| 2017/0148318 A1* | 5/2017 | Eckman | G08G 1/0962 |
| 2018/0157980 A1* | 6/2018 | Kochura | G06N 5/048 |
| 2019/0213429 A1* | 7/2019 | Sicconi | G06F 3/0346 |
| 2021/0011545 A1* | 1/2021 | Min | G06F 3/011 |

OTHER PUBLICATIONS

Wikipedia, "Homicidal sleepwalking", printed on Jul. 24, 2019, 7 pages.
Jaslow, "More than 8.4 million Americans sleepwalk each year, study finds", CBS News, May 15, 2012, 4 pages.
Broussard, "New Apple Patent Describes Sleep Tracking System With Bedtime Ritual Sensing and Power Nap Function", Macrumors, Jun. 27, 2017, 11 pages.

* cited by examiner

PREVENTING ACCESS TO POTENTIALLY HAZARDOUS ENVIRONMENTS

BACKGROUND

The present invention relates generally to the field of computing, and more particularly to communication and security.

In more recent history, stress, a highly active life, and a lack of balance between personal life and work have caused the general public to develop habits that may directly affect a human's well-being. Such habits, in particular accessing one or more potentially dangerous hazards in a physical environment, may be harmful for the user.

SUMMARY

Embodiments of the present invention disclose a method, computer system, and a computer program product for managing a plurality of electronic devices controlling access to one or more hazards in a physical environment. The present invention may include detect a plurality of brain-wave patterns associated with a user. The present invention may then include, in response to detecting motion of the user and the plurality of brain-wave patterns associated with the user matching a pattern, operating at least one electronic device from the plurality of electronic devices to disable access to a hazard (i.e., corresponding hazard). The present invention may further include operating the at least one electronic device from the plurality of electronic devices to enable access to the corresponding hazard based on receiving input from the user to enable the at least one electronic device from the plurality of electronic devices, wherein the input being received from the user is in response to prompting the user to correctly respond to a question previously answered by the user.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
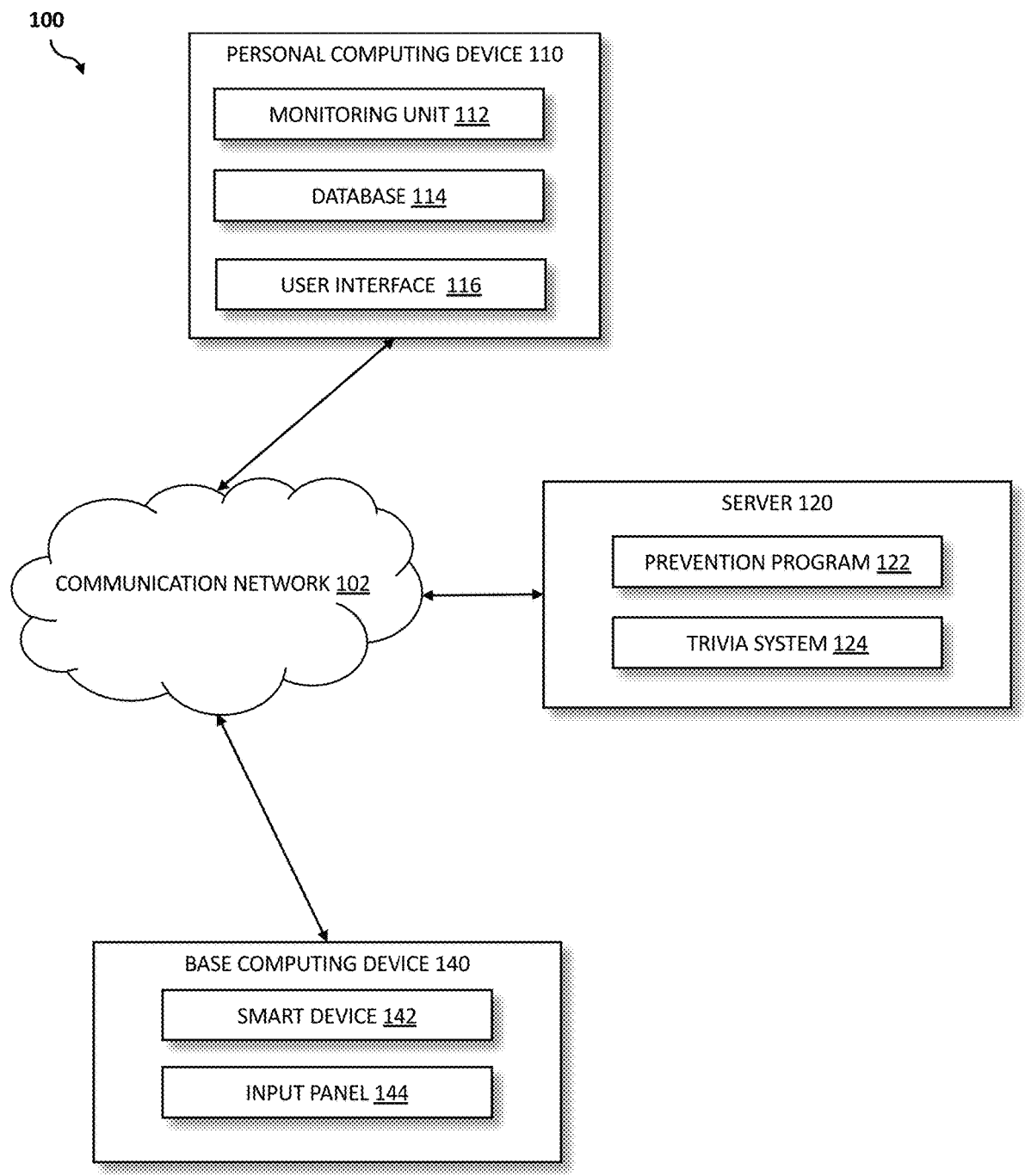
FIG. 1 illustrates a networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language, python programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed concurrently, substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for managing a plurality of electronic devices controlling access to one or more hazards in a physical environment. As such, the present embodiment has the capacity to improve the technical field of computing by utilizing detected brain wave patterns to confirm or deny the disablement or enablement of access to a plurality of smart devices associated with corresponding hazards in a physical environment. More specifically, the prevention program may detect a brain wave pattern of a user. The prevention program may then operate at least one electronic device to disable access to a corresponding hazard, solely in response to detecting a motion of a user in addition to the brain pattern of a user matching a desired pattern. Further, the prevention program may also operate the at least one electronic device to enable access to the corresponding hazard based on receiving a request of enablement from an authenticated user. In the present invention, authentication of a user may be executed through analysis of the user's response to the prompted question of the present invention. When the response is determined correct, the user may then be authenticated.

As previously described, in more recent history, stress, a highly active life, and a lack of balance between personal life and work have caused the general public to develop habits that may directly affect a human's well-being. Such habits, in particular accessing one or more potentially dangerous hazards in a physical environment, may be harmful for the user. Traditional methods have failed to stop people from accessing these potentially dangerous situations.

Therefore, it may be advantageous to, among other things, implement a system to manage a plurality of electronic devices controlling access to one or more hazards in a physical environment, where such access is confirmed by the detected desired brain patterns of a user in combination with a detected motion of the user.

According to at least one embodiment, a prevention program may obtain data about a brain activity state of a user utilizing a plurality of Internet of Things (i.e., IoT) devices. In such embodiment, the plurality of IoT devices utilized by the prevention program may detect rapid eye movement (i.e., REM) occurrences from non-REM (i.e., NREM) from awakenings. Such plurality of IoT devices may further differentiate slow wave sleep from any other type of NREM occurrences (i.e., SWS). SWS may be characterized by high amplitude low frequency brain activity. In such state of sleep, only one hemisphere of the user's brain may be asleep, leaving the motor functions available to the body. The available motor functions may allow the user to enter into a potentially dangerous environment. Dangerous environments may be defined as areas containing dangerous objects (e.g., a closet with cleaning products, a room with electrical equipment).

According to at least one embodiment, a prevention program may transmit information obtained about a brain activity of a user associated with a computing device via a communication network. Brain activity information, in such embodiment, may include the name of the device from which the brain activity of the user was obtained in addition to the detected brain wave pattern of the user. In such embodiment, brain wave patterns (i.e., waves) detected may include at least one of alert wakefulness, relaxed wakefulness, NREM N1, NREM N2, NREM 4, REM. In such embodiment, the communication network may be a Bluetooth® (i.e., Bluetooth and all Bluetooth-based trademarks and logos are trademarks or registered trademarks of Bluetooth SIG, Inc. and/or its affiliates) connection or an application programming interface (i.e., API) connection.

According to at least one embodiment, in response to a monitoring unit detecting a desired predefined wave pattern associated with a user in current time, a prevention program may commence the recording of a motion of a user utilizing a plurality of IoT devices associated with a computing device. In such embodiments, the plurality of IoT devices may be associated with the user (e.g., resident to a smart watch) or associated with another IoT device remotely located to a user (e.g., resident to a motion detector located on the ground).

In at least one embodiment, in response to detecting the motion of a user utilizing a plurality of IoT devices, a prevention program may command a plurality of devices to be disabled. In such embodiment, a personal computing device (e.g., a smart watch) may transmit commands to a base computing device (e.g., a smart house) via a communication network. In such embodiment, the plurality of devices commanded to be disabled may include doors, windows, hazardous areas, valves, switches, or electrical systems. In such embodiment, hazardous areas may be predefined by a user. In at least one other embodiment, a prevention program may command a personal computing device (e.g., a smart watch) to determine and map hazardous areas of the physical environment. Restricting access to such hazardous areas may prevent a user from accessing dangerous areas containing dangerous objects (e.g., a closet with cleaning products), eating without full consciousness, or activating electrical equipment that requires fully conscious monitoring (e.g., a gas stove). In such embodiment, the prevention program may obtain a list of the plurality of devices commanded to be disabled, adding or removing a plurality of devices from the obtained list of the plurality of devices commanded to be disabled, changing the name of a plurality of devices from the updated obtained list of the plurality of devices commanded to be disabled, obtaining the current lock status (e.g., enabled, disabled) of the plurality of devices commanded to be disabled and changing the lock status of the plurality of devices commanded to be disabled.

According to at least one embodiment, in response to detecting the user has commanded for the plurality of devices previously commanded to be disabled to now be enabled, the prevention program may prompt the user with a question requiring a response (i.e., an answer). In the embodiment, the answer may be pre-defined by a user at a previous time. In general, users detected with a certain brain wave pattern may not access the memory area of the brain to correctly respond to the request for an answer to a prompted question. In embodiments, the user may input the answer onto a personal computing device that may then be transferred via a communication network to a base computing device in which the prevention program may be stored. In at least one other embodiment, the user inputting the requested answer may input such answer directly onto the base computing device (e.g., an input panel of a smart house).

In at least one other embodiment, the prevention program may run a trivia system that requests a user to answer a prompted question. In such embodiment, the trivia system may store pre-defined questions in which the user needs to correctly answer to enable access to the plurality of smart devices previously disabled. Answers to such pre-defined questions may be obtained when the user of the prevention program is detected to have a desired brain wave pattern, wherein such brain wave pattern indicates both hemispheres of the brain are active. In such embodiment, the user may input correctly defined answers to a personal computing device (e.g., a smartwatch) that may then be transferred to a base computing device associated with the physical environment (e.g., a smart house). In at least one other embodiment, the user may input correctly defined answers directly to a base computing device in which the prevention program is stored. In further embodiments, users may input answers on a computing device that may then be stored in a database locally located to the prevention program or remotely located to the prevention program.

In at least one embodiment, a prevention program may analyze the requested answer obtained by the user. In such embodiments, a prevention program may compare the input obtained by the user against the pre-defined correct answer input by the user.

According to at least one embodiment, in response to determining the answer input by the user is correct, a prevention program may enable the plurality of devices previously disabled. In such embodiment, the prevention program may obtain a list of the plurality of devices previously commanded to be disabled, removing a plurality of devices from the obtained list of the plurality of devices previously commanded to be disabled, obtaining the current lock status of the plurality of devices previously commanded to be disabled, and furthermore, changing the lock status of the plurality of devices previously commanded to be disabled. Such commands may be communicated to the prevention program from a direct or indirect computing device via a communication network.

Referring to FIG. 1, an exemplary networked computer environment 100 in accordance with one embodiment is depicted. In the example embodiment, the networked computer environment 100 includes a personal computing device 110, a server 120, and a base computing device 140, interconnected via a communication network 102. While, in the example embodiment, programming and data of the present invention are stored and accessed remotely across several servers via the communication network 102, in other embodiments, programming and data of the present invention may be stored locally on as few as one physical computing device or amongst other computing devices than those depicted.

In the example embodiment, the communication network 102 is a communication channel capable of transferring data between connected devices. In the example embodiment, the communication network is the Internet, representing a worldwide collection of networks and gateways to support communications between devices connected to the Internet. Moreover, the communication network 102 may include, for example, wired, wireless, or fiber optic connections which may be implemented as an intranet network, a wide area network (WAN), a local area network (LAN), a telecommunication network, a wireless network, a public switched network, a satellite network, or a combination thereof. In general, the communication network 102 can be any combination of connections and protocols that will support communications between the personal computing device 110, the server 120, and the base computing device 140. In the example embodiment, communications between the plurality of computing devices of the networked computer environment 100 utilize application programming interface (i.e., API) communication.

In the example embodiment, the personal computing device 110 includes a monitoring unit 112, a database 114, and a user interface 116, and may be a server, a laptop computer, a netbook computer, a personal computer (PC), a desktop computer, a server, a personal digital assistant (PDA), a rotary phone, a touchtone phone, a smart phone, a mobile phone, a virtual device, a thin client, a smart watch, a smart headband, or any other electronic device or computing system capable of receiving and sending data to and from other computing devices. While, in the example embodiment, the computing device is shown as a single device, in other embodiments, the personal computing device 110 may be comprised of a plurality of computing devices, working together or working separately. In various embodiments, the networked computer environment 100 may include one or more of the personal computing device 110, wherein a user of the personal computing device 110 may send data to the server 120 or the base computing device 140. In general, the personal computing device 110 monitors unit brain wave patterns, monitoring changes in the physical environment of the user, receiving and sending data to and from a user, and storing data for the use of the prevention program.

In the example embodiment, the monitoring unit 112 may be comprised of a combination of devices, subsystems, or modules wherein the combination of these devices measure events or detect changes in the environment in which the plurality of devices is being used. Devices utilized in the example embodiment, may include IoT sensors, biometric sensors, accelerometers, or motion detectors. In some embodiments, the monitoring unit 112 may communicate with other devices in the networked computer environment 100 to transfer data, trigger a commencement of data collection, or command programs to run. In the example embodiment, the data collected from the monitoring unit may be stored locally on the personal computing device 110. In other embodiments, the data collected may be stored remotely and accessed via the communication network 102. In the example embodiment, the monitoring unit 112 may be used to detect brain activity of the user, motion of the user, a physiological state of the user, or environmental changes. In the example embodiment, the monitoring unit 112 may be a plurality of electrodes capable of performing an electroencephalography to detect brain activity, a motion detector capable of detecting a user's motion, a biometric sensor capable of converting the biometric trait of a user into electrical signals, or a camera capable of detecting changes in the local environment of a user. The monitoring unit 112 may be comprised of a cluster or plurality of computing devices, working together, or working separately.

In the example embodiment, the database 114 is a collection of files including but not limited to, hypertext markup language (i.e., HTML) files, cascading style sheets (i.e., CSS) files, extensible markup language (i.e., XML) files, and JavaScript files. In general, the database 114 is comprised of the one or more corresponding hazards in association with the smart device 142 controlling enablement/disablement of the corresponding hazard (e.g., a closet with chemicals is associated with a door A). Additionally, the database 114 may store question data and associated answer data.

In the example embodiment, the user interface 116 allows the user of the personal computing device 110 to interact with the internal processes of the personal computing device 110 and the communication capabilities of the device via the communication network 102. In general, the input panel 144 is used to obtain and transfer input and output data to and from the plurality of devices, which may include the server 120 and the base computing device 140.

In the example embodiment, the server 120 includes a prevention program 122 and a trivia system 124, and is a device that is capable of communicating with the personal computing device 110 and the base computing device 140 via the communication network 102. As will be discussed with reference to FIG. 4, the server 120 may include internal components 902 and external components 904a, respectively. The server 120 may also operate in a cloud computing service model, such as Software as a Service (SaaS), Analytics as a Service (AaaS), Platform as a Service (PaaS), or Infrastructure as a Server (IaaS). The server 120 may be located in a cloud computing deployment model, such as a private cloud, community cloud, public cloud, or hybrid cloud.

The prevention program 122, in the example embodiment, is a software application that is capable of disabling and enabling a plurality of devices that may correspond to a plurality of deemed hazards to a user of the personal computing device 110, the server 120, or the base computing device 140. Further, such software application is capable of obtaining data collected from remote computing devices via the communication network 102, transferring obtained data to the personal computing device 110, the base computing device 140, and the server 120, requesting data from a user of the personal computing device 110, the server 120, or the base computing device 140, and moreover, upon detection of a request to enable such plurality of devices, analyzing the data obtained from such request. In the example embodiment, the prevention program 122 is further, a program that supports communications between one or more users of the personal computing device 110, the server 120, or the base computing device 140. In the example embodiment, the prevention program 122 is accessed via the communication network 102 by a user of the personal computing device 110 or a user of the base computing device 140.

In the example embodiment, the trivia system 124 is a database that which contains a collection of files including, but not limited to, HTML files, CSS files, XML files, and JavaScript files. In general, the trivia system 124 is comprised of pre-defined questions to transfer to the user of the personal computing device 110 or the base computing device 140 upon request by the prevention program 122. Requests to obtain data within such database from the prevention program 122 come about when a user inputs a request to enable access to the plurality of the smart device 142 (i.e., the smart devices) that have been previously disabled. In such embodiment, the trivia system 124 stores the pre-defined questions in association with the correct answer. In the example embodiment, the correct answer may be a cognitive password set by the prevention program 122 (e.g., 6542354). In other embodiments, the correct answer may be a personalized answer (e.g., the name of the user's pet). In further embodiments, the correct answer may be a generic answer. Generic answers may be defined as answers known to the general public (e.g., the sky is blue).

In the example embodiment, the base computing device 140 includes a smart device 142 and an input panel 144 and may be a server, a laptop computer, a netbook computer, a personal computer (PC), a desktop computer, a server, a personal digital assistant (PDA), a rotary phone, a touchtone phone, a smart phone, a mobile phone, a virtual device, a thin client, or any other electronic device or computing system capable of receiving and sending data to and from other computing devices. While, in the example embodiment, the base computing device 140 is shown as a single device, in other embodiments, the base computing device 140 may be comprised of a cluster or plurality of computing devices, working together or working separately. In various embodiments, the networked computer environment 100 may include one or more of the base computing device 140, wherein a user of the personal computing device 110 may send data to the personal computing device 110 or the server 120. In general, the base computing device 140 is capable of transmitting obtained and received data to and from the plurality of the smart device 142 associated with the identified hazards via communications with the communication network 102. The base computing device 140 is also capable of understanding and interpreting input from a user of the personal computing device 110 or the server 120.

In the example embodiment, the smart device 142 may be any device capable of communication with the prevention program 122 via the communication network 102. The smart device 142 is a device, in such embodiment, that is capable of being enabled or disabled to allow or deny access to an identified hazard. The smart device 142 may control a door, a cabinet door, a window, a gate, a valve, a button, or a switch.

It should be appreciated that FIG. 1 provides only an illustration of one implementation and does not imply any limitations with regard to the environments in which different embodiments may be implemented. Many modifications to the depicted environments may be made based on design and implementation requirements.

According to the present embodiment, a user using a personal computing device 110 or a server 120 (respectively) may use the prevention program 122 to prevent the user from gaining access to hazards. The prevention method is explained in more detail below with respect to FIG. 2.

Figure 2:
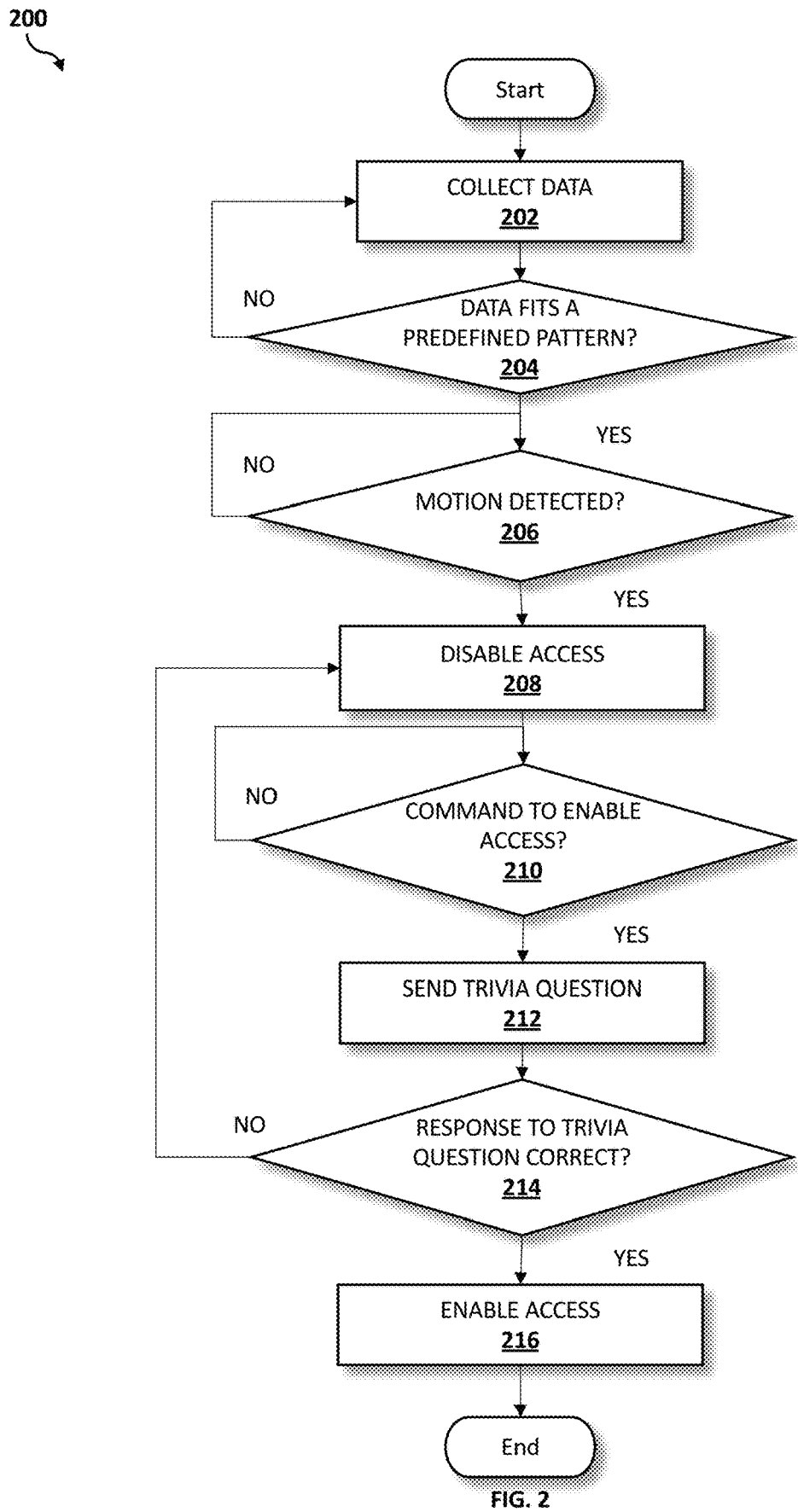
FIG. 2 is an operational flowchart illustrating a process for a prevention program of the networked computer environment according to at least one embodiment.

Referring now to FIG. 2, an operational flowchart 200 illustrating the exemplary networked computer environment 100 used by the prevention program 122 according to at least one embodiment is depicted.

At 202, data is collected. In at least one embodiment, the prevention program 122 may obtain data about the brain wave patterns (i.e., patterns, brain patterns) of a user utilizing the monitoring unit 112 of the personal computing device 110. In such embodiments, the monitoring unit 112 may include a plurality of Internet of Things (IoT) devices or biometric sensors, which may include, image sensors, motion detection sensors, accelerometer sensors, and temperature sensors. Patterns obtained may indicate rapid eye movement occurrences (i.e., REM), non-rapid eye movement occurrences (i.e., NREM), or awakenings, more specifically, alert wakefulness, relaxed wakefulness, NREM N1, NREM N2, NREM N3, NREM N4, or REM.

In the example embodiment, the personal computing device 110 may transfer the obtained pattern data from the monitoring unit 112 of the personal computing device 110 to the prevention program 122 of the server 120 via the communication network 102. Obtained pattern data communicated to the server 120 may include the name of the device in which the brain activity of the user was obtained (e.g., a headband) in addition to the detected pattern of the user.

In the example embodiment, the prevention program 122 may simultaneously obtain preferred pattern data. Preferred pattern data, in general, may be defined as the pattern of brain waves desired by a user to further the prevention program 122 process. In the example embodiment, preferred pattern data may be selected with reference to a desired amplitude of brain waves (e.g., 5 mm), a desired low frequency (e.g., 0.5 Hz), a desired high frequency (e.g., 50 Hz), a desired difference in frequencies (e.g., 0.45 Hz). Preferred pattern data may also be selected based on instantaneous data (e.g., data collected at a specific time) or may be chosen based on interval data (e.g., data collected between desired time one and desired time two). Furthermore, preferred pattern data may be selected with reference to a combination of both physical attributes of the data (e.g., frequencies, amplitudes) and time, (e.g., 20 minutes of frequency 50 Hz followed by 10 minutes of frequency 30 Hz). In the example embodiment, preferred pattern data may be obtained from the database 114 of the personal computing device 110. In such embodiment, the database 114 may be updated prior to the activation of the prevention program 122 by the user of the personal computing device 110 or a unique user related to the user (e.g., a caretaker). In other embodiments, preferred pattern data may be obtained from the input panel 144 of the base computing device 140. In such embodiments, a user unique of the user of the computing device (e.g., a caretaker) may select or input a preferred pattern in real time to further the process of the prevention program 122. Inputting a preferred pattern may make use of a graphical user interface (i.e., GUI). In such embodiments, the GUI may require a predefined file format for the input file to be of. In further embodiments, the GUI may obtain a plurality of input file formats and convert such input files as necessary.

In some embodiments, the personal computing device 110 may transfer the obtained preferred pattern data from either the database 114 of the base computing device 140 or the input panel 144 of the computing device to the prevention program 122 of the server 120 via the communication network 102. Preferred pattern data, in such embodiment, may include, the title of the user whom selected or input the preferred pattern (e.g., a doctor) in addition to the chosen preferred pattern.

In some embodiments, the data obtained may be transferred to one or more of the personal computing device 110, the server 120 and the base computing device 140, where users unique to the user of the personal computing device 110 may be able to monitor the collected patterns of the user.

For example, User B, the primary physician of User A, has updated the database to save the preferred pattern for User A as the NREM N1 pattern. Subsequently, User B has updated the database to select corresponding hazards: Room 1, Outside 1, Closet 1, and Bathroom 2. After utilizing monitoring units on the headband of User A, the prevention program 122 receives data that reads 'The headband of User A detects the User A is currently experiencing a NREM N1 pattern'. At this time, the data obtained from the headband of User A is displayed to User B.

Then, at 204, the prevention program 122 determines whether the collected data from a brain of a user fits a certain predefined pattern. In the example embodiment, the prevention program 122 may compare the collected pattern data to the preferred pattern data. In such embodiment, the prevention program 122 may obtain the collected data of a user and may compare the two patterns. The prevention program 122 may then identify discrepancies between the two patterns to determine if the collected data of a user fits a certain predefined pattern. Identification of discrepancies, in the example embodiment, may utilize image analysis wherein the two obtained patterns are images (e.g., superimposed EEG images). In other embodiments, the prevention program 122 may utilize a numerical comparator to determine if the collected data of a user fits a certain predefined pattern. The numerical comparator, for example, may obtain numerical values associated with the plurality of brain wave patterns (e.g., frequencies, amplitude measurements) and may compare the corresponding numerical values to determine if the collected data of a user fits a certain predefined pattern. In the example embodiment, the discrepancy between the two patterns may need to reach a threshold to accurately determine the obtained pattern does not fit the preferred pattern. Thresholds may be defined as the minimum or maximum value that must be exceeded upon comparison of two or more objects for the prevention program 122 to determine the obtained pattern does not fit the preferred pattern and may be percentages (e.g., 10% difference of wave amplitude height), or integers (e.g., a difference of 10 cycles/sec, a difference of 1 mm in wave amplitude). In other embodiments, any discrepancy between the compared patterns may trigger the prevention program 122 to determine the collected data of a user does not fit a certain predefined pattern.

Continuing with the previous example, the obtained pattern from User A, NREM N1 is then compared to the preferred pattern of the database, input by the User B, NREM N1. The wave pattern of User A is superimposed to the NREM N1 pattern selected by User B.

If the prevention program 122 determines the obtained patterns of the user fail to match the chosen preferred pattern at 204 (decision 204, "NO" branch), the prevention program 122 returns back to collect data at 202 to re-evaluate the brain patterns of the user.

If the prevention program 122 determines the obtained patterns of the user matches the chosen preferred pattern at 204 (decision 204, "YES" branch), the prevention program 122 determines whether motion of the user has been detected at 206. In at least one embodiment, the monitoring unit 112 of the personal computing device 110 may monitor for acceleration of the user. In such embodiments, the monitoring unit 112 may utilize an accelerometer associated with the personal computing device 110 of the user. In general, the monitoring unit 112 when at rest may not feel any internal horizontal forces applied to components of the monitoring unit 112. In the example embodiment, wherein the monitoring unit 112 is positioned relative to the user (e.g., on the wrist of the user) the monitoring unit 112 may send a signal to the prevention program 122 via the communication network 102 upon detection of an internal horizontal force (e.g., a force caused by walking forward). In further embodiments, the monitoring unit 112 may utilize a camera in combination with image analysis to detect motion of a user. In such further embodiments, the monitoring unit 112 of the personal computing device 110 may be located in the surrounding environment of the user (e.g., the floor). In such embodiments, the monitoring unit 112 may send a signal to the prevention program 122 via the communication network 102 upon detection of any change in user position relative to the physical environment (e.g., detection of a User A at location A at time A, then User A at location B at time B).

In furthering the previous example, the prevention program 122 is capable of determining that the obtained pattern from User A matches the preferred pattern of the database determined previously by User B. At this time, the accelerometer of the headband of User A begins recording the motion of the User A. The User A, then, jumps three steps forward.

If the prevention program 122 determines the user has not moved at 206 (decision 206 "NO" branch), the prevention program 122 returns to 206 to re-evaluate the motion of the user. In at least one other embodiment, the prevention program 122 may continuously monitor the brain wave pattern of the user. If the prevention program 122 determines the brain wave pattern of the user has changed from the initial collection of brain wave patterns of a user, the prevention program 122 may return to 202 to recollect data of the user.

If the prevention program 122 determines the user has accelerated at 206 (decision 206 "YES"), access is disabled at 208. In at least one embodiment, the prevention program 122 may disable access to a corresponding hazard utilizing the smart device 142 associated with the corresponding hazard. Corresponding hazards, in general, may be locations or devices defined as hazardous to a user at the time in which the pattern of the user matches the selected preferred pattern. Generally, the smart device 142 associated with a corresponding hazard may allow or deny access to the corresponding hazard and may be a door, a cabinet door, a window, a gate, a valve, a button, or a switch.

In some embodiments, a user may select smart devices prior to the activation of the prevention program 122 to be disabled by a user of the personal computing device 110, the server 120, or the base computing device 140. Data associated with the smart devices and the corresponding hazards, in such embodiment, may be stored in the database 114. In other embodiments, where the smart devices are not selected prior to activation, the prevention program 122 may request input from the input panel 144 of the base computing device 140 for a user unique to the user of the personal computing device 110 to select the plurality of smart devices to be disabled. Data regarding the smart devices and the corresponding hazards may then be stored in the database 114.

In other embodiments, the prevention program 122 may automatically select the smart devices after determining which corresponding hazards may be hazardous to the user of the personal computing device 110. In such embodiment, the prevention program 122 may base the determination of hazards on user obtained patterns, preferred patterns, time of day (e.g., A.M., P.M.), type of corresponding hazard (e.g., the outdoors, a closet, a room), and plurality of corresponding hazards available for disablement. Such corresponding hazards may then be stored in the database 114. In further embodiments, the prevention program 122 may select all the available smart devices.

In some embodiments, the prevention program 122 may parse through the database 114 to obtain an identifier corresponding with the smart device 142 associated with each selected corresponding hazard (e.g., Door A, Window B). Identifiers may include a unique combination of letters, numbers, or symbols (e.g., a device serial number). The prevention program 122 may, subsequently, command the plurality of the smart device 142 associated with the plurality of selected corresponding hazards to be disabled (e.g., lock Door A). In at least one embodiment, commands may be communicated from the prevention program 122 of the server 120 to the smart devices of the base computing device 140 via the communication network 102.

In reference to the previous example, the accelerometer associated with the headband of User A detects the User A has jumped three steps forward. As previously described, User B selects Room 1, Outside 1, Closet 1, and Bathroom 2 to be disabled upon detection of acceleration and a NREM N1 brain wave pattern. The prevention program 122 then obtains the smart device 142 associated with each selected corresponding hazard. The prevention program 122 then commands the smart devices obtained to be disabled. In such example, the Door A of Room 1, the Window A of Outside 1, the Door B of Closet 1, and the Door C of Bathroom 2 are now disabled.

Then, at 210, the prevention program 122 determines whether the prevention program 122 has been commanded to enable access to the identified plurality of hazards. In at least one embodiment, commands to enable access may be manually input by a user of the personal computing device 110, the server 120, or the base computing device 140. Manual input may include, verbally expressing a command, flipping a switch, pushing a button, or turning a dial. Manual input, in such embodiments, executed on the personal computing device 110 or the base computing device 140 may include manual input data transferred to the prevention program 122 of the server 120 for analysis of input. In embodiments, manual input may use a GUI. In the present embodiment, the prevention program 122 may use natural language processing (NLP) or speech recognition to further analyze manual input.

If the prevention program 122 determines no commands have been input to enable access to the plurality of hazards at 210 (decision 210, "NO" branch), the prevention program 122 returns to decision 210 to reexamine the presence of input.

If the prevention program 122 determines a command has been input to enable access to the plurality of hazards at 210 (decision 210, "YES" branch), a trivia question (i.e., trivia, question) is sent at 212. In the example embodiment, the prevention program 122 may locally send an alert to the trivia system 124 of the server 120. The alert may include the name or identification of the computing device used to input the requested response, as well as the name of the user (e.g., User A).

In the present embodiment, the trivia system 124 may select a question to send to the computing device of the user. Questions may be cognitive (e.g., "Please enter the pin."), generic (e.g., "Please enter the color of the sky."), or personalized (e.g., "Please enter the name of your first pet.").

In some embodiments, where no user information is identified, a cognitive or generic question may be selected by the trivia system 124. Answers to cognitive questions may be generated automatically and presented to the user upon installation of the trivia system 124, prior to activation. In other embodiments, answers to cognitive questions may be input by a user before activation of the prevention program 122. Answers to cognitive questions may be stored locally within the trivia system 124. In other embodiments, answers to cognitive questions may be transferred and stored remotely within the database 114 of the personal computing device 110 via the communication network 102.

In some embodiments, answers associated with a selected generic question may be stored within the trivia system 124. In other embodiments, answers associated with a selected generic question may be transferred and stored in the database 114 of the personal computing device 110 via the communication network 102.

In other embodiments, where user information has been previously stored, (e.g., the name of the user's first pet), a personalized question may be selected. User information (i.e., question answers), in the present embodiment, may be linked to the user and stored in the database 114. Such information may be manually input by a user of the personal computing device 110, the server 120, or the base computing device 140, before, after, or during the activation of the prevention program 122.

In the present embodiment, the prevention program 122 may include an opt-in/opt-out feature in which the user may select to opt-in to or opt-out of the collection of data associated with the specific user. The opt-in/opt-out feature may be changed at any time, and if the user opts in to the prevention program 122, then the user may be notified when the data collected is activated and the data collection has commenced. In some embodiments, the user may limit when data is collected, how the data is collected, what type of data is collected and the purposes for which the data collected is utilized. The user may also limit how and where the data is stored.

In other embodiments, the trivia system 124 may select multiple questions to be communicated to the user.

Subsequent to selecting a question to communicate to the user, the trivia system 124 may, in the example embodiment, communicate the selected question to the user of the computing device upon which the manual request to access the plurality of devices was made. In other embodiments, the trivia system 124 may communicate the selected question to all computing devices within the networked computer environment 100. In further embodiments, the trivia system 124 may prompt the user to select a desired computing device of the networked computer environment 100 for the question to be sent to.

In furthering the previous example, User A flips a switch on the wall-mounted input panel to request enablement of the smart devices associated with the corresponding hazards. Such enablement request is sent to the prevention program 122. The trivia system 124 sends, after receiving a command from the prevention program 122, a request back to the wall-mounted input panel that reads "Please type in the pin received upon setup."

Then, at 214, the prevention program 122 determines whether the answer to the question is correct. In at least one embodiment, the trivia system 124 may receive the response of the user to the question previously communicated to the user via the communication network 102.

In such embodiments, the trivia system 124 may simultaneously obtain the correct answer to the question. In at least one embodiment, the correct answer to the communicated question may be found within the trivia system 124. In other embodiments, the correct answer to the communicated question may be found in the database 114 on the personal computing device 110, in which the trivia system 124 may utilize the communication network 102.

In embodiments, the trivia system 124 may transmit both the received response of the user and the correct answer to the prevention program 122. In the example embodiment, the prevention program 122 may use data analysis to determine whether the received response and the correct answer are identical (i.e., determine whether the received response is the correct answer). Data analysis may consist of discriminating answers at a syntactical level. In another embodiment, the prevention program 122 may perform deeper analysis to further understand the received response. Deeper analysis may include machine learning algorithms, such as natural language processing, to determine whether the input may be synonymous to the correct answer. The prevention program 122 may, upon deeper analysis, for example, parse through a thesaurus definition of the correct answer to identify any synonymous possible answers. For example, the prevention may determine "dog" and "puppy" to be two different answers upon first analysis. After deeper analysis, the prevention program 122 determines "puppy" to be a more specific subset of the correct answer, "dog". Moreover, the prevention program 122 is able to determine such answer is correct. In other embodiments, any discrimination between the received response of the user and the correction answer may cause the prevention program 122 to determine the response is not correct. In embodiments, the user, upon initial input of the correct answer (e.g., predefining the correct answer), may select to accept or deny synonymous answers upon triggering of the trivia system 124.

In embodiments, if the prevention program 122 does not receive any input from the user, the prevention program 122 determines the response to be incorrect, therefore, returning to 208 to ensure the smart devices are disabled. In the example embodiment, the prevention program 122 may determine the user has not responded if the user does not respond to the request in an allocated amount of time. The allocated amount of time set for the user to respond may be set by a user of the personal computing device 110 or the base computing device 140 prior to the activation of the prevention program 122. In other embodiments, the allocated amount of time set for the user to respond may be automatically set to a definite amount of time (e.g., five minutes).

In the example embodiment, the remaining allocated time may be displayed to the user. In other embodiments, the prevention program 122 may verbally alert the user of the remaining time to respond. In further embodiments, the prevention program 122 may not alert the user of the remaining allocated time.

In at least one embodiment, the trivia system 124 may be capable of determining whether the received response and the correct are identical, without use of the prevention program 122.

In furthering the previous example, the User A inputs '512634' into the wall-mounted input panel. The trivia system 124 simultaneously obtains the correct answer to the communicated cognitive question by parsing through the database 114, the database in which the question and answer had been linked and stored upon setup. The trivia system 124 obtains from the database 114 the pin '512634'.

If the prevention program 122 determines the received response is not correct at 214 (decision 214 "NO" branch), the prevention program 122 returns to 208 to ensure access of the plurality of the smart device 142 of the base computing device 140 is disabled.

If the prevention program 122 determines the received response is correct at 214 (decision 214 "YES" branch), access is enabled at 216. In at least one embodiment, the prevention program 122 may enable access to the plurality of corresponding hazards utilizing the smart devices that may have been previously disabled. The prevention program 122 may parse through the database 114 to determine the enablement status of the smart devices associated with the corresponding hazards. The prevention program 122 may, in such embodiment, parse through and obtain the smart device 142 associated with each disabled corresponding hazard. Subsequently, the prevention program 122 may command each obtained smart device to be enabled (e.g., unlock door A). In at least one embodiment, commands may be communicated from the prevention program 122 of the server 120 to the smart devices of the base computing device 140 via the communication network 102.

With reference to the previous enumerated example, the prevention program 122 receives the user response '512634' and compares the user response against the obtained answer from the database 114 '512634'. The prevention program 122 determines there is no distinction between the two and therefore, such received response is correct. The prevention program 122 parses through the database 114 to find that Room 1, Outside 1, Closet 1, and Bathroom 2 are disabled. The prevention program 122 obtains the smart devices previously commanded to disable access to the corresponding hazards. Obtained smart devices include: the Door A of Room 1, the Window A of Outside 1, the Door B of Closet 1, and the Door C of Bathroom 2. Commands are then sent, via the communication network 102, to the Door A, Window A, Door B, and Door C to command each smart device to enable access to the corresponding hazard.

As another example, a User C desires the search of REM brain-wave patterns to activate the prevention program 122. The prevention program 122 recognizes that User D is experiencing REM patterns and has activated the accelerometer of his/her smart watch. The smart-watch communicates with a pre-programmed representational state transfer (REST) API of the plurality of the smart device 142 of the smart house to disable access to doors inside the house, hazardous areas previously defined through the smart-watch application, as well as any turn-on electrical systems or gas leaks. The prevention program 122 receives the following REST API endpoints of the smart devices around the house from the smart watch:

get a list of the plurality of the smart device 142 (i.e., configured items) api\devices_configuration (GET)

get a list of the current devices with the option to add new device api\devices_configuration\device_id (GET\POST)

list/change the plurality of the smart device 142 mode (disabled, enabled) api\device_mode(GET\POST)

The following JavaScript Object Notation (JSON) message is then sent to the smart-house REST API to execute the disablement process.

import requests
import json
import os
import sys
url='127.0.0.1\api\device_mode\'
data={"Mode: "REM", "action": "Disable", "source": "Smartwatch","
device_name": "door_1, cabinet_1, cabinet_2, outlet_a, outlet_b, freezer"}
data_json=json.dumps(data)
headers={'Content-type': 'application/json'}
response=requests.post(url, data=data_json, headers=headers)

User D then executes a house enablement request. Furthermore, the smartwatch of the User D sends a trivia question to User D. User D responds to the trivia question. The prevention program 122 then analyzes the response and upon detecting the response is correct, issue the enablement JSON message to the smart-house REST API as follows:

url='127.0.0.1\api\device_mode\'
data={"Mode: "REM", "action": "Enable", "source": "Smartwatch", "
device_name": "door_1, cabinet_1, cabinet_2, outlet_a, outlet_b, freezer")
data_json=json.dumps(data)
headers=('Content-type': 'application/json'}
response=requests.post(url, data=data_json, headers=headers)

In another embodiment, the prevention program 122 may utilize machine learning. After multiple activations of the prevention program 122, a machine learning algorithm may obtain, analyze, store, and learn the wave patterns associated with a user. Such algorithm may learn to automatically recognize the wave patterns of the user being in an affected state (i.e., a state wherein the obtained pattern of the user fits the selected predefined pattern). In such embodiment, the prevention program 122 may continuously collect and analyze the brain wave patterns of the user. Therefore, overtime, the prevention program 122 may eliminate the use of the trivia question previously used to confirm the state of the user.

It may be appreciated that FIG. 2 provides only an illustration of one embodiment and do not imply any limitations with regard to how different embodiments may be implemented. Many modifications to the depicted embodiment(s) may be made based on design and implementation requirements.

The functionality of a computer may be improved by the prevention program 122 because the prevention program 122 may detect a plurality of brain-wave patterns associated with a user. In response to determining the user has moved and has a brain wave pattern matching the predefined pattern, the prevention program 122 may be able to operate at least one of the electronic devices to disable access to a corresponding hazard. The prevention program 122 may further advance current technology by operating the at least one of the plurality of electronic devices to enable access to the corresponding hazard. Operation of such electronic device may be based on received input from the user to enable the at least one of the plurality of electronic devices. The prevention program 122 may function to enable the at least one of the plurality of electronic devices wherein input being received from the user is in response to the prompting of the user to correctly respond to a question previously answered by the user.

Figure 3:
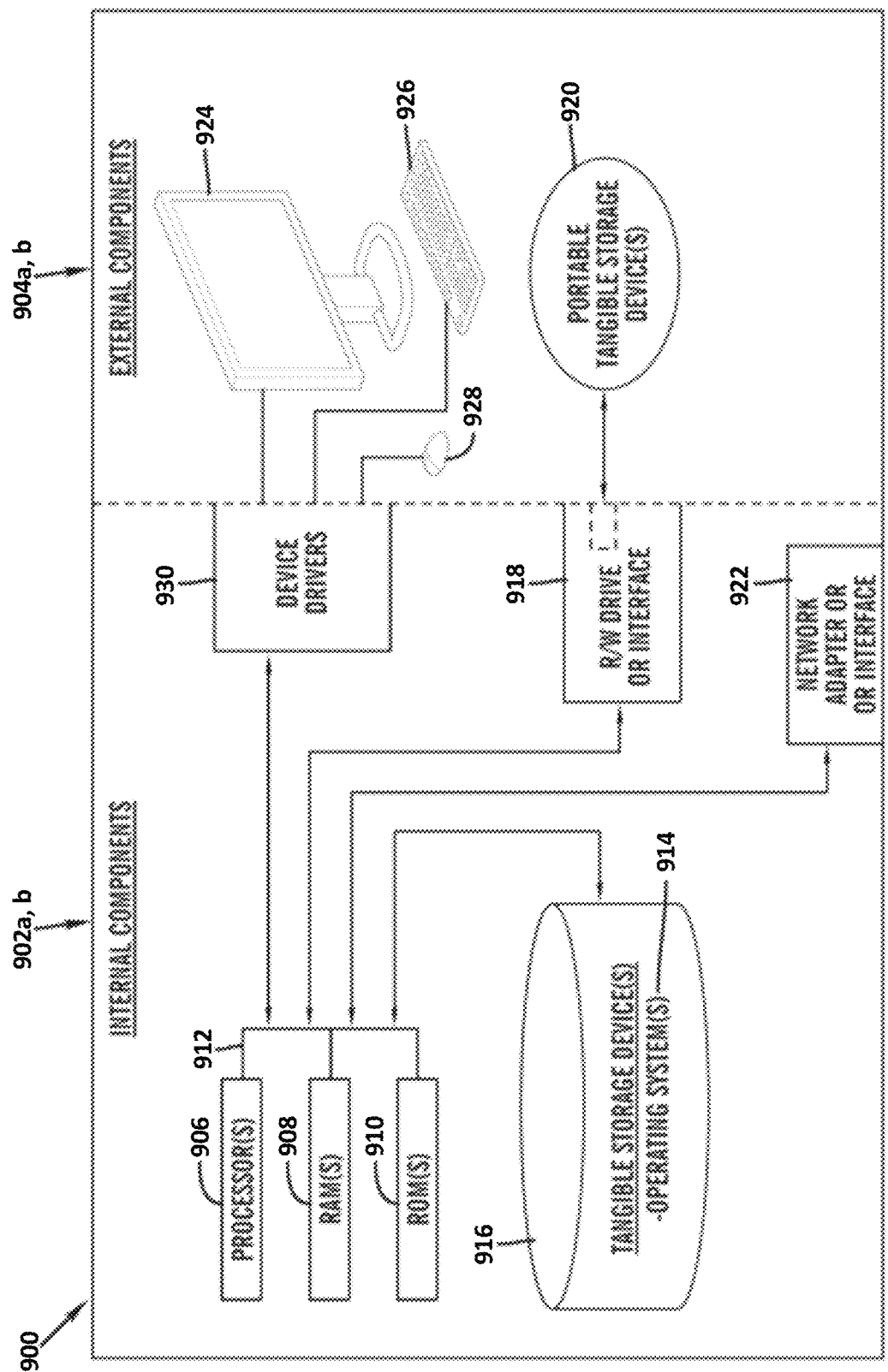
FIG. 3 is a block diagram of internal and external components of computers and servers depicted in FIG. 1 according to at least one embodiment.

FIG. 3 is a block diagram 900 of internal and external components of computers depicted in FIG. 1 in accordance with an illustrative embodiment of the present invention. It should be appreciated that FIG. 3 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

The personal computing device 110, the server 120, the base computing device 140, and the communication network 102 may include respective sets of internal components 902 *a, b* and external components 904 *a, b* illustrated in FIG. 3. Each of the sets of internal components 902 *a, b* includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the prevention program 122 of the server 120, and the trivia system 124 of the server 120 may be stored on one or more computer-readable tangible storage devices 916 for execution by one or more processors 906 via one or more RAMs 908 (which typically include cache memory). In the embodiment illustrated in FIG. 3, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902 *a, b* also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the prevention program 122 can be stored on one or more of the respective portable computer-readable tangible storage devices 920, read via the respective R/W drive or interface 918 and loaded into the respective hard drive 916.

Each set of internal components 902 *a, b* may also include network adapters (or switch port cards) or interfaces 922 such as a TCP/IP adapter cards, wireless wi-fi interface cards, or 3G or 4G wireless interface cards or other wired or wireless communication links. The prevention program 122 of the server 120 and the trivia system 124 of the server 120 can be downloaded from an external computer (e.g., server) via a network (for example, the Internet, a local area network or other, wide area network) and respective network adapters or interfaces 922. From the network adapters (or switch port adaptors) or interfaces 922, the prevention program 122 of the server 120 and the trivia system 124 of the server 120 are loaded into the respective hard drive 916. The network may comprise copper wires, optical fibers, wireless transmission, routers, firewalls, switches, gateway computers and/or edge servers.

Each of the sets of external components 904 *a, b* can include a computer display monitor 924, a keyboard 926, and a computer mouse 928. External components 904 *a, b* can also include touch screens, virtual keyboards, touch pads, pointing devices, and other human interface devices. Each of the sets of internal components 902 *a, b* also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Analytics as a Service (AaaS): the capability provided to the consumer is to use web-based or cloud-based networks (i.e., infrastructure) to access an analytics platform. Analytics platforms may include access to analytics software resources or may include access to relevant databases, corpora, servers, operating systems or storage. The consumer does not manage or control the underlying web-based or cloud-based infrastructure including databases, corpora, servers, operating systems or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
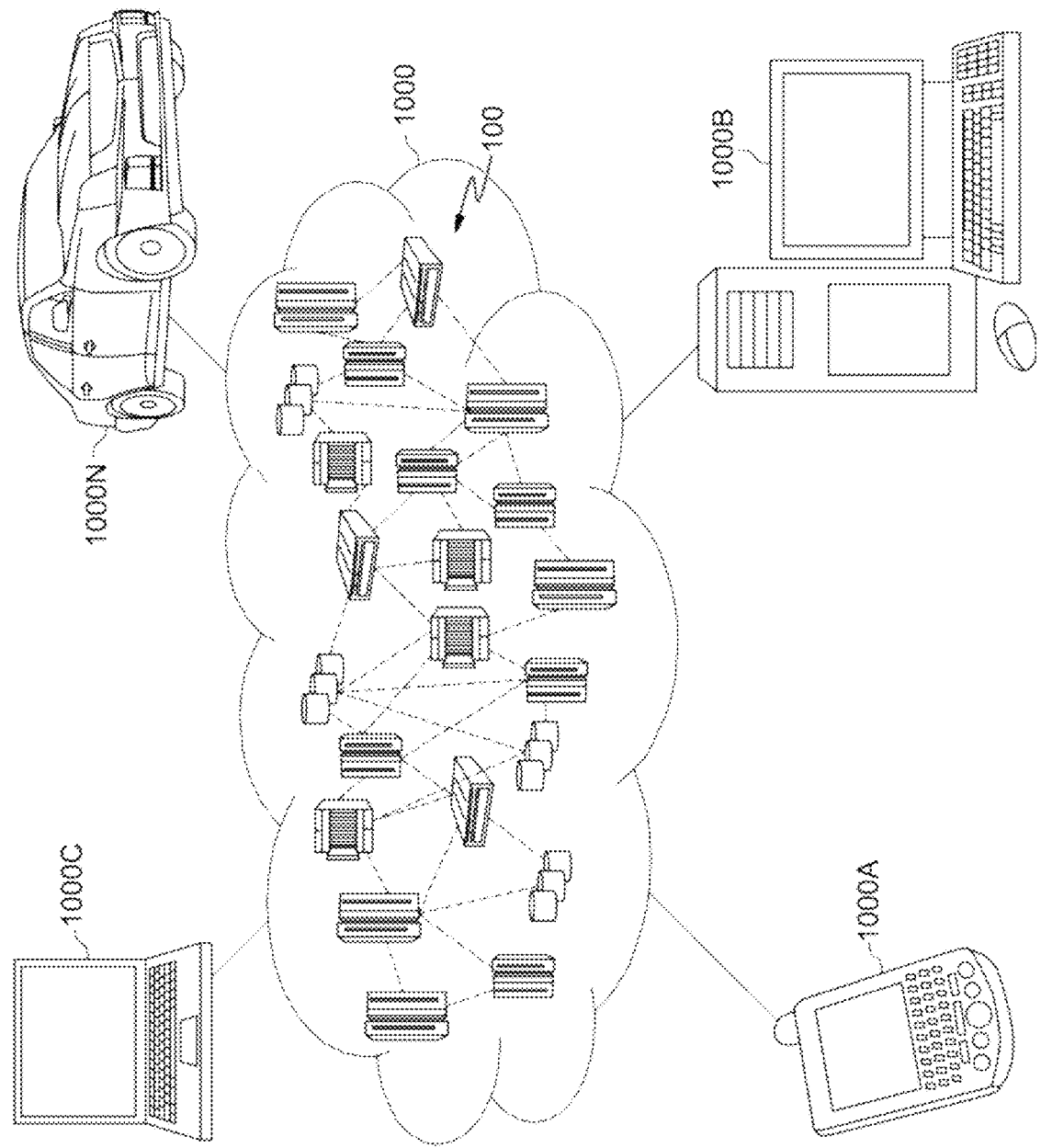
FIG. 4 is a block diagram of an illustrative cloud computing environment including the computer system depicted in FIG. 1, in accordance with an embodiment of the present disclosure.

Referring now to FIG. 4, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 4 are intended to be illustrative only and that computing nodes 100 and cloud computing environment 1000 can communicate with any type of computerized device over any type of network and/or network addressable connection (e.g., using a web browser).

Figure 5:
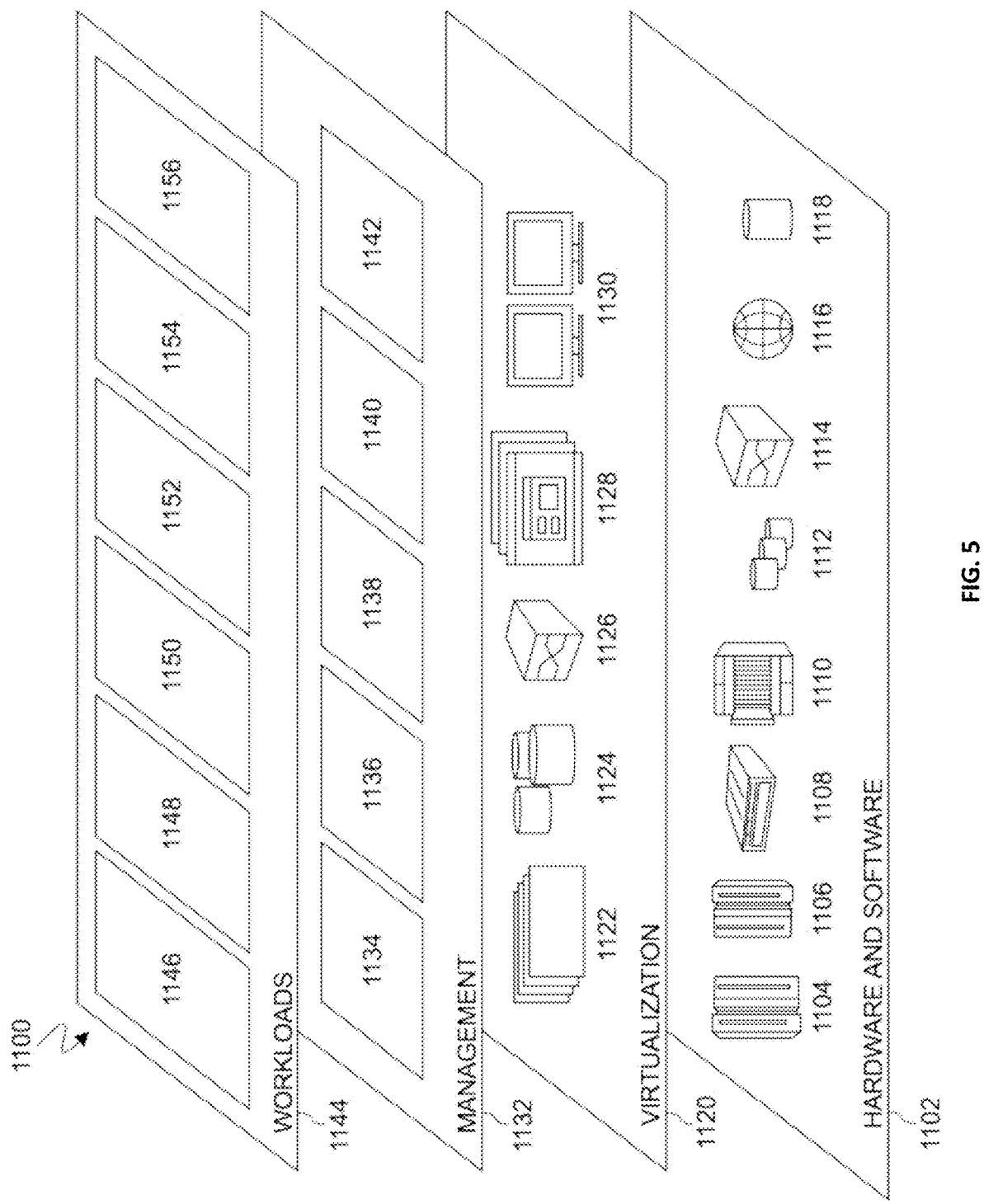
FIG. 5 is a block diagram of functional layers of the illustrative cloud computing environment of FIG. 4, in accordance with an embodiment of the present disclosure.

Referring now to FIG. 5, a set of functional abstraction layers 1100 provided by cloud computing environment 1000 is shown. It should be understood in advance that the components, layers, and functions shown in FIG. 5 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and a prevention program 1156. A prevention program 1156 presents a way to manage a plurality of electronic devices controlling access to one or more hazards in a physical environment.

The descriptions of the various embodiments of the present invention have been presented for purposes of illustration but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
   detecting a plurality of brain-wave patterns associated with a user;
   in response to detecting motion of the user and a plurality of brain-wave patterns associated with the user matching a pattern, operating at least one electronic device from a plurality of electronic devices to disable access to a corresponding hazard; and
   operating at least one electronic device from the plurality of electronic devices to enable access to the corresponding hazard based on receiving input from the user to enable access to the at least one electronic device from the plurality of electronic devices;
   wherein the at least one electronic device previously disabled access to the corresponding hazard;
   wherein the input being received from the user is in response to prompting the user to correctly respond to a question previously answered by the user.

2. The method of claim 1, wherein detecting motion of the user, furthering comprises:
   detecting an acceleration associated with the user by utilizing a plurality of monitoring electronic devices.

3. The method of claim 1, wherein detecting the plurality of brain-wave patterns associated with the user, further comprises:
   receiving the detected plurality of brain-wave patterns by utilizing the plurality of monitoring electronic devices; and
   comparing the received plurality of brain-wave patterns to a preferred pattern.

4. The method of claim 3, wherein the preferred pattern is defined by the user prior to activation of the plurality of monitoring electronic devices utilized to detect the plurality of brain-wave patterns associated with the user.

5. The method of claim 1, wherein operating the at least one electronic device from the plurality of electronic devices to disable access to the corresponding hazard, further comprises:
   automatically identifying the corresponding hazard in a physical environment;
   determining the at least one electronic device from the plurality of electronic devices is capable of denying access to the corresponding hazard; and
   disabling the determined at least one electronic device from the plurality of electronic devices capable of denying access to the corresponding hazard.

6. The method of claim 1, wherein prompting the user to correctly respond to the question, further comprises:
   determining the at least one of the plurality of electronic devices associated with the user inputting a request to enable access of the previously disabled at least one electronic device from the plurality of electronic devices is capable of denying access to the corresponding hazard; and
   displaying the question on the determined at least one electronic device from the plurality of electronic devices associated with the user input request to enable access.

7. The method of claim 1, wherein prompting the user to correctly respond to the question previously answered by the user, further comprises:
   comparing the received input to an answer previously provided by the user; and
   in determining the prompted input matches the answer previously provided by the user, enabling access of the at least one electronic device from the plurality of electronic devices capable of allowing access to the corresponding hazard.

8. A computer system for managing a plurality of electronic devices controlling access to one or more hazards in a physical environment, comprising:
   one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:
   detecting a plurality of brain-wave patterns associated with a user;
   in response to detecting motion of the user and the plurality of brain-wave patterns associated with the user matching a pattern, operating at least one electronic device from the plurality of electronic devices to disable access to a corresponding hazard; and
   operating the at least one electronic device from the plurality of electronic devices to enable access to the corresponding hazard based on receiving input from the user to enable access to the at least one electronic device from the plurality of electronic devices;
   wherein the at least one electronic device previously disabled access to the corresponding hazard;

wherein the input being received from the user is in response to prompting the user to correctly respond to a question previously answered by the user.

9. The computer system of claim 8, wherein detecting motion of the user, furthering comprises:
   detecting an acceleration associated with the user by utilizing a plurality of monitoring electronic devices.

10. The computer system of claim 8, wherein detecting the plurality of brain-wave patterns associated with the user, further comprises:
   receiving the detected plurality of brain-wave patterns by utilizing the plurality of monitoring electronic devices; and
   comparing the received plurality of brain-wave patterns to a preferred pattern.

11. The computer system of claim 10, wherein the preferred pattern is defined by the user prior to activation of the plurality of monitoring electronic devices utilized to detect the plurality of brain-wave patterns associated with the user.

12. The computer system of claim 8, wherein operating the at least one of the plurality of electronic devices to disable access to the corresponding hazard, further comprises:
   automatically identifying the corresponding hazard in a physical environment;
   determining at least one electronic device from the plurality of electronic devices is capable of denying access to the corresponding hazard; and
   disabling the determined at least one electronic device from the plurality of electronic devices capable of denying access to the corresponding hazard.

13. The computer system of claim 8, wherein prompting the user to correctly respond to the question, further comprises:
   determining at least one electronic device from the plurality of electronic devices associated with the user inputting a request to enable access of the previously disabled at least one electronic device from the plurality of electronic devices is capable of denying access to the corresponding hazard; and
   displaying the question on at least one electronic device from the plurality of electronic devices associated with the user input request to enable access.

14. The computer system of claim 8, wherein prompting the user to correctly respond to the question previously answered by the user, further comprises:
   comparing the received input to an answer previously provided by the user; and
   in determining the prompted input matches the answer previously provided by the user, enabling access of the at least one of the plurality of electronic devices capable of allowing access to the corresponding hazard.

15. A computer program product for managing a plurality of electronic devices capable of controlling access to one or more hazards in a physical environment, comprising:
   one or more computer-readable storage media and program instructions stored on at least one of the one or more tangible storage media, the program instructions executable by a processor to cause the processor to perform a method comprising:
      detecting a plurality of brain-wave patterns associated with a user;
      in response to detecting motion of the user and the plurality of brain-wave patterns associated with the user matching a pattern, operating at least one electronic device from the plurality of electronic devices to disable access to a corresponding hazard; and
      operating the at least one electronic device from the plurality of electronic devices to enable access to the corresponding hazard based on receiving input from the user to enable access to the at least one electronic device from the plurality of electronic devices;
      wherein the at least one electronic device previously disabled access to the corresponding hazard;
      wherein the input being received from the user is in response to prompting the user to correctly respond to a question previously answered by the user.

16. The computer program product of claim 15, wherein detecting motion of the user, furthering comprises:
   detecting an acceleration associated with the user by utilizing a plurality of monitoring electronic devices.

17. The computer program product of claim 15, wherein detecting the plurality of brain-wave patterns associated with the user, further comprises:
   receiving the detected plurality of brain-wave patterns by utilizing the plurality of monitoring electronic devices; and
   comparing the received plurality of brain-wave patterns to a preferred pattern.

18. The computer program product of claim 17, wherein the preferred pattern is defined by the user prior to activation of the plurality of monitoring electronic devices utilized to detect the plurality of brain-wave patterns associated with the user.

19. The computer program product of claim 15, wherein operating the at least one electronic device from the plurality of electronic devices to disable access to the corresponding hazard, further comprises:
   automatically identifying the corresponding hazard in a physical environment;
   determining the at least one electronic device from the plurality of electronic devices is capable of denying access to the corresponding hazard; and
   disabling the determined at least one electronic device from the plurality of electronic devices capable of denying access to the corresponding hazard.

20. The computer program product of claim 15, wherein prompting the user to correctly respond to the question, further comprises:
   determining the at least one electronic device from the plurality of electronic devices associated with the user inputting a request to enable access of the previously disabled at least one electronic device from the plurality of electronic devices is capable of denying access to the corresponding hazard; and
   displaying the question on at least one electronic device from the plurality of electronic devices associated with the user input request to enable access.

* * * * *